(12) United States Patent
Kim et al.

(10) Patent No.: US 6,733,786 B1
(45) Date of Patent: May 11, 2004

(54) SOMATOTROPIN COMPOSITION WITH IMPROVED SYRINGEABILITY

(75) Inventors: Nam Joong Kim, Taejon-si (KR); Je Phil Ryoo, Taejon-si (KR)

(73) Assignee: LG Chem Investment, Ltd., Seoul (KR)

( * ) Notice: Subject to any disclaimer, the term of this patent is extended or adjusted under 35 U.S.C. 154(b) by 0 days.

(21) Appl. No.: 09/926,590

(22) PCT Filed: Oct. 16, 2000

(86) PCT No.: PCT/KR00/01151

§ 371 (c)(1), (2), (4) Date: Nov. 21, 2001

(87) PCT Pub. No.: WO01/70256

PCT Pub. Date: Sep. 27, 2001

(30) Foreign Application Priority Data

Mar. 24, 2000 (KR) .................................... 2000-0015091

(51) Int. Cl.⁷ ................................................. A61K 9/14
(52) U.S. Cl. ........................ 424/486; 424/484; 424/485; 424/422
(58) Field of Search .................... 424/422, 484, 424/450, 485, 486; 514/458

(56) References Cited

U.S. PATENT DOCUMENTS 6,254,884 B1 * 7/2001 Kim et al. .................. 424/450
6,497,886 B1 * 12/2002 Breitenbach et al. ....... 424/401

* cited by examiner

Primary Examiner—Thurman K. Page
Assistant Examiner—Liliana Di Nola-Baron
(74) Attorney, Agent, or Firm—Jacobson Holman PLLC

(57) ABSTRACT

The present invention relates to an improved somatotropin composition consisting of somatotropin having in vivo, at least one of lipid-soluble vitamins and at least one of pharmaceutically acceptable lubricants, which improves poor syringeability under cold temperature which has been a defect of the conventional somatotropin formulation using vitamins, and which shows at least the equivalent effect to that of the conventional formulation.

20 Claims, No Drawings

US 6,733,786 B1

SOMATOTROPIN COMPOSITION WITH IMPROVED SYRINGEABILITY

This is a nationalization of PCT/KR00/01151 filed Oct. 16, 2000 and published in English.

FIELD OF THE INVENTION

The present invention relates to a composition containing somatotropin having activity in vivo, and particularly, to a composition which can obtain the sustained release effect of the pharmaceutical to avoid the inconvenience of daily administration as well as have the suitable syringeability for being parenterally administered into animals to solve problems during injection, in which somatotropin is mixed with excipients.

DESCRIPTION OF THE PRIOR ART

Recently, somatotropin which can be produced in a large scale by using recombinant DNA technology according to development of genetic engineering has been commercially available for increasing the productivity of milk in cattle, and has been studied for improving feed efficiency and meat quality in swine.

Most of formulations developed hitherto for administering somatotropin having activity in vivo are simply the long acting types wherein a large amount of somatotropin is administered to avoid the inconvenience of daily administration. For example, U.S. Pat. No. 5,411,951 and U.S. Pat. No. 5,474,980 disclose sustained release formulations prepared by adding a gelling agent such as aluminum monostearate into vegetable oil; by gelling the oil by heating; and by mixing somatotropin or other drugs with it homogeneously, because drugs become phase-separated and precipitated in short time when only vegetable oil is used. These techniques have been already used to prepare the sustained release formulations of various drugs such as known antibiotics(U.S. Pat. No. 2,491,537, U.S. Pat. No. 2,507,193 and U.S. Pat. No. 3,016,330), pamoate salts of oxazepines(U.S. Pat. No. 3,676,557) or relaxin which is a kind of hormone(U.S. Pat. No. 2,964,448), adrenocorticotropic hormone(U.S. Pat. No. 3,869,549), luteinizing hormone releasing factor(U.S. Pat. No. 4,256,737), gonadotropin(U.S. Pat. No. 3,852,422) and insulin(U.S. Pat. No. 2,143,590, U.S. Pat. No. 2,174,862, U.S. Pat. No. 2,882,203, U.S. Pat. No. 2,920,014 and U.S. Pat. No. 3,102,077) and the like.

There are similar prior art techniques using oil simply for preparing sustained release formulations. For example, EP 211691 discloses that somatotropin is mixed with a mixture of wax and oil and EP 213851 discloses that the sustained release formulation is prepared by mixing somatotropin with a mixture of oil and commercially available glyceride release-modifying agent. Also, EP 314421 discloses that sustained release formulations of somatotropin are prepared by adding absorption controlling material(e.g., calcium stearate and dextran) to oil. But these are also the formulations wherein the active ingredients in the known injectable formulations containing oil used for other drugs have been substituted with somatotropin.

In addition, the sustained release techniques without using oil have been attempted. For example, in EP 193917, somatotropin was mixed with water-soluble carbohydrate polymer(e.g., starch, dextrin) to improve the sustained release effect. However, it has shorter duration of action than formulations mixed in oil, and it may do harm on stability of somatotropin due to its water-solubility.

Different techniques from the above-mentioned techniques have been attempted for lengthening duration of action of somatotropin formulations. U.S. Pat. No. 4,861,580 discloses that the sustained release formulation of somatotropin was prepared as a liposome type by using lipid-soluble materials such as alphatocopherol hemisuccinate Tris salt, phosphatidyl choline and phosphatidyl ethanolamine. And in U.S. Pat. No. 4,675,189, the sustained release formulation of somatotropin was prepared as a microcapsule type by using biocompatible polymer. And in U.S. Pat. No. 4,857,506, the sustained release formulation of somatotropin was prepared as a multiple water-in oil-in water(W/O/N) emulsion type. But somatotropin formulations according to these techniques are inadequate to be commercialized since the formulations have short duration of action or very complicated manufacturing processes requiring high techniques, and low stability as well as low recovery rate of making somatotropin into a desired form.

By using quite different techniques, implantable formulations, which are solid dosage forms, were prepared for improving the sustained release of somatotropin. These techniques have been described in U.S. Pat. No. 4,452,775, U.S. Pat. No. 4,761,289, U.S. Pat. No. 4,765,980, U.S. Pat. No. 4,774,091, U.S. Pat. No. 4,786,501, U.S. Pat. No. 4,863,736, U.S. Pat. No. 5,035,891, U.S. Pat. No. 5,198,422, U.S. Pat. No. 5,228,697, U.S. Pat. No. 5,356,635, U.S. Pat. No. 5,595,752 and EP 246540 and 462959, and PCT/US92/01877, PCT/US91/08129, PCT/US90/01340, PCT/AU87/00139 and the like. These techniques tried to secure sustained release of somatotropin by implanting somatotropin into the animal body by surgical operation using an expensive device, or implanting a compressed somatotropin form into the animal body using a special implant apparatus. These implanting techniques are preferred for obtaining a desirable release amount and sustained effect of somatotropin. However, the implanting process is too difficult to be performed on animals and animals also feel very uncomfortable due to the foreign substance.

U.S. Pat. No. 5,520,927 and Korean Patent No. 177306 attempted to lengthen duration of action of somatotropin using tocopherol acetate which has been used as an antioxidant to prevent oxidation reaction of drugs which may occur in a somatotropin composition simply containing oils as described above. However, since the viscosity of tocopherol acetate or vitamin A dramatically increases as the temperature decreases, the somatotropin composition shows such poor syringeability that cannot be used in winter or cold areas, or immediately after being taken out of a refrigerator which is the storage condition of the somatotropin composition. Thus, it needs several tens of minutes to melt the composition under ambient temperature before use. Further, the syringeability under ambient temperature is not so good that it requires the great effort and long time for injection of the composition, resulting in doubling the pain of animal being administered.

The inventors of the present invention have conducted intensive researches to solve the above-mentioned problems of conventional somatotropin formulations.

SUMMARY OF THE INVENTION

The present inventors have developed a somatotropin-containing composition which can be administered into the body by injection that is the most general administration method hitherto as well as which can be injected with superior syringeability, even in winter at lower temperatures or immediately after being taken out of a refrigerator which is the storage condition of a somatotropin composition, and which has the same or better sustained release effect and physiological activity of somatotropin as those of conventional somatotropin formulations. The composition of the present invention is inherently in suspension form and consists of somatotropin, at least one lipid-soluble vitamin and at least one pharmaceutically acceptable lubricant.

An object of the present invention is to provide a composition comprising somatotropin and vitamins with improved syringeability, which can be more easily administered into body by injection that is the most general administration method hitherto, which can decrease injection frequency resulting in reducing the labor and cost for administration as well as animals pain, and which can increase the reproduction efficiency and the productivity of milk according to administration of somatotropin, while decrease the incidence of mastitis and metabolic diseases, by administering somatotropin with vitamins simultaneously, not separately.

Another object of the present invention is to provide a composition comprising somatotropin, which can be used in cold areas or in winter as well as immediately after being taken out of a refrigerator that is the storage condition of somatotropin composition, and which can be administered without difficulty due to of its improved syringeability under room temperature.

In accordance with the present invention, there is provided a composition consisting of somatotropin, at least one of lipid-soluble vitamins and at least one of pharmaceutically acceptable lubricants. The present invention has many advantages, including providing a composition containing somatotropin with improved syringeability. These and other features, aspects, and advantages of the present invention will become better understood with reference to the following description and appended claims.

DETAILED DESCRIPTION

The present invention provides a composition consisting of somatotropin, at least one of lipid-soluble vitamins and at least one of pharmaceutically acceptable lubricants. The present invention will hereinafter be described in more detail. The vitamins to be mixed with somatotropin in the present composition are lipid-soluble vitamins, such as vitamin A or vitamin E, which are preferred drugs in preparing a mixed formulation since they can make protein drugs such as somatotropin stable by delaying the drugs from binding with water.

In addition to the above-described advantage of the formulation, vitamin A increases the sense of vision, particularly dark adaptation in relation with rhodopsin and iodopsin, the visual dyes in rods and cones which sensitize light in the retina. It also improves abnormal dryness, degeneration, keratinization and ulceration of mucus, xerophthalmia and keratomalacia and increases the resistance against various diseases. In addition, it has been reported to be an essential element for maintenance of epithelial tissue and the growth of bone and teeth and to have a growth stimulating activity.

Vitamin E deficiency in animals causes the white muscle disease which partly changes the color of muscle fiber into gray and makes the muscles atrophied. Initial symptoms of muscular atrophy is that the entire body loses its flexibility and appears to be stiff, and gradually becomes week and paralyzed, and then difficulty in breathing occurs. As the disease progresses, animals having severe symptoms become unable of lactation. Also, vitamin E is referred as an anti-sterility vitamin because it overcomes the sterility of animals, and it stimulates growth of animals. In addition, vitamin E helps normal reproduction processes, prevents the abnormal development of muscle and may prevent cerebromalacia, irregular activity of muscle, muscle spasm, ataxia and tonic spasm.

Hitherto, somatotropin compositions have been developed considering only the productivity and reduction of administration frequency for target animals. For example, somatotropin compositions have been designed for dairy cow, focusing on increase of the productivity of milk and reduction of the dairy farmer's labor according to the frequent administration by lengthening the in vivo duration of action of somatotropin. However, if somatotropin compositions have been administered into animals, focusing only on productivity, without considering the health conditions of animals, it may often cause side effects. The incidence of diseases such as mastitis which is a major disease of dairy cow occurs mainly due to environmental factors and hygienic factors when milking, however, it has been also reported that the incidence frequency of mastitis depends on the ability of, each dairy cow. That is, it is known that mastitis more often occurs in more milk-productive cows than less milk-productive cows. Therefore, when somatotropin is used to increase the milk productivity, proper treatment according to each cow's milk productivity, as well as clean milking condition, is necessary to prevent the incidence of mastitis. There are many factors to cause the mastitis as mentioned above. Thus, it is preferred to increase dairy cows' resistance against bacteria as a countermeasure for prevention of mastitis. To this end, proper farm cares would be important. However, such prevention effect can be obtained by providing appropriate drugs, for example, vitamins. That is, when vitamin A or vitamin E is deficient, the mucous epithelial cells of teat canal, teat cistern and the like become keratinized, which induces the infection and proliferation of bacteria. The proliferated bacteria invade the gland cistern, resulting in severe mastitis. In addition, they lower the synthesis of immunoglobulin and keratin which are protecting materials in interior teat canal, thereby causing serious mastitis.

There are several methods for examining the mastitis, but the general method is to count the number of somatic cells in milk The criterion for diagnosis is the number of somatic cells per 1 ml of milk, which determines level of mastitis. The lower the number, the better the milk, then the milk is recognized as having been produced from a dairy cow without mastitis.

Therefore, the present invention has prepared compositions containing somatotropin, which increase the productivity of milk, enhance the health of target animals by minimizing side effects which might be caused by the increase of milk productivity, and maximize convenience of the diary farmer who administers the compositions into animals by improving the syringeability markedly without affecting the physiological activity of the protein drug, somatotropin.

Among the lipid-soluble vitamins, particularly vitamin A may cause side effects when administered in a large amount. Thus, the formulations should be prepared with extra care. The effects of the somatotropin and the vitamins can be maximized when an appropriate amount of the vitamins is added to the composition.

In the composition of the present invention, the pharmaceutically acceptable lubricant may be one which can be mixed with the lipid-soluble vitamins and the lubricant may be used alone or in a mixture of at least two lubricants.

The lubricants for improving syringeability of the composition which are the core of the present invention are pharmaceutically acceptable materials which do not affect the physiological activity of somatotropin. In the composition of the present invention, the pharmaceutically acceptable lubricants may include pharmaceutically acceptable alcohol or its derivatives, preferably benzyl alcohol, ethyl alcohol, isopropyl alcohol, butyl alcohol, or the like. In the composition of the present invention, the pharmaceutically acceptable lubricants also include esters of fatty acid and alcohol, such as ethyl oleate, isopropyl myristate, isopropyl laurate, isopropyl lanolate, isopropyl palmitate, or the like; unsaturated fatty acids, for example, liquid unsaturated fatty acids, such as oleic acid, linoleic acid, linolenic acid, or the like; esters of acid and aromatic alcohol, such as benzyl benzoate or the like; and other materials which can be mixed with the lipid-soluble vitamins such as polyoxyethylene alkyl ether (bridges), tetrahydrofurfuryl alcohol polyethylene glycol ether sold under the trademark GLYCOFUROL™ (c.f. "Handbook of Pharmaceutical Excipients"), derivatives of polyethylene glycol, glycerin, or the like. It is preferable that the pharmaceutically acceptable lubricant in the present invention is one which can be mixed with the lipid-soluble vitamins. The lubricants in the present invention include pharmaceutically acceptable materials which can be well mixed with lipid-soluble vitamins, particularly vitamin A or vitamin E or derivatives thereof, to improve the syringeability. Such lubricant may be used alone or in a mixture of at least two lubricants.

Somatotropin which can be used in the composition of the present invention may be generally the somatotropin of various animals, but bovine somatotropin or porcine somatotropin is preferred. Also, in the composition of the present invention, natural somatotropin purified highly from the pituitary gland of animals or somatotropin produced artificially by recombinant DNA technology can be used.

In the composition of the present invention, the lipid-soluble vitamin may be vitamin A or its derivative, or vitamin E or its derivative. In the composition of the present invention, vitamin A or its derivative, which does not affect the physiological activity of somatotropin, for examples, any type of optical isomer of vitamin A, vitamin A acetate, vitamin A palmitate, vitamin A propionate, etc., can be used. Also, vitamin E or its derivative, which does not affect the physiological activity of somatotropin, for examples, any type of optical isomer of vitamin E, vitamin E acetate, vitamin E succinate, vitamin E nicotinate, vitamin E phosphate, etc., can be used in the composition of the present invention.

In the composition of the present invention, the somatotropin is preferably present in an amount of from 10 to 50% by weight based on the total weight of the composition, In the composition of the present invention, vitamin A or its derivative is preferably present in an amount of from 100,000 to 5,000,000 vitamin A units and more preferably from 300,000 to 3,500,000 vitamin A units per 1 g of somatotropin. In the composition of the present invention, vitamin E or its derivative is preferably present in an amount of from 500 to 12,000 vitamin E units and more preferably from 1,500 to 8,500 vitamin E units per 1 g of somatotropin. In the composition of the present invention, the lubricant may be preferably present in an amount of from 0.5 to 25% by weight and more preferably from 1 to 15% by weight, based on the total weight of the composition.

In preparing the composition of the present invention, somatotropin in a powder form may be prepared by lyophilizing a somatotropin solution alone, or by lyophilizing fine particles prepared by adding a pharmaceutical excipient (e.g., lecithin, etc.) to a somatotropin solution, or by lyophilizing the mixture of a somatotropin solution with a stabilizing agent such as sucrose, mannitol, trehalose and the like. When the lyophilized somatotropin powder is used, water content and particle size should be considered. It is preferable that the water content is 3% or below for the stability of somatotropin. The particle size which is related to phase-separation after long storage and syringeability of the composition, is preferably 10 $\mu$m or below. When the particle size of the lyophilized somatotropin is bigger than the desired size, it will be necessary to carry out ball mill or air jet mill process in order to reduce the particle size, without changing the quality of the somatotropin. For example, the mixed composition of somatotropin and vitamins may be prepared by homogeneously mixing the somatotropin powder with an appropriate amount of lipid-soluble vitamins. Then, the composition of the present invention may be prepared by homogeneously mixing the mixture with an appropriate amount of pharmaceutically acceptable lubricants. Alternatively, the composition of the present invention may be prepared by homogeneously mixing the somatotropin with lipid-soluble vitamins and pharmaceutically acceptable lubricants. It will be apparent to those skilled in the art that the composition of present invention may be formulated into any appropriate dosage form, and may be administered in any appropriate manner.

The previously described versions of the present invention have many advantages, including providing somatotropin-containing injectable compositions with improved syringeability under the ambient temperature and cold temperature which maximize the convenience in administering somatotropin into animals' body by injection; and providing somatotropin-containing injectable compositions which can increase the reproduction efficiency and the milk productivity, while prevent the incidence of mastitis and metabolic diseases in cow and the like according to the increase of milk productivity, by administering somatotropin with lipid-soluble vitamins, particularly vitamin A, vitamin E or the like simultaneously.

The present invention will now be described in more detail in connection with the following examples, which should be considered as being exemplary only and not limiting the present invention.

EXAMPLE 1

3000 ml of bovine somatotropin(LG Chemical Ltd. Biotech Research Institute) solution(130.5 mg/ml) was divided into three lyophilization trays by 1000 ml respectively and lyophilized in a freeze-dryer for about 48 hours. The lyophilized powder was ground using an airjet mill to make particles of average 8 $\mu$m size of diameter. Thus obtained bovine somatotropin in a powder form had 1.4% of water content, which was measured in a heating-type moisture analyzer.

Then the lyophilized bovine somatotropin powder was homogenously mixed with vitamin E acetate(1 g=1,000 unit, ROCHE) and benzyl alcohol in a homogenizer, according to the amount described below in Table 1.

2 g of each homogenously mixed composition was taken to fill in a polypropylene syringe of 9.8 mm size of diameter having a 16-gauge needle of 1.7 cm size of length to prepare a sample for measuring syringeability. The prepared samples were stored under ambient temperature(22° C.) and cold temperature(4° C.) for 24 hours. The syringeability was measured by proceeding in a rate of 7.8 cm per minute using a syringeability measuring device(Test Stand Model 2252 and CPU gauge 9500 series, Aikoh Engineering, Japan) at each temperature. The measured results were shown in Table 1.

TABLE 1

| Amount of *bST (g) | Amount of vitamin E acetate (g) | Amount of benzyl alcohol (g) | Syringeability(kgf) Ambient temp. | Cold temp. |
|---|---|---|---|---|
| 5.00 | 15.00 | 0 | 5.24 | 14.76 |
|  | 14.70 | 0.30 | 4.65 | 10.72 |
|  | 14.25 | 0.75 | 2.86 | 10.01 |
|  | 14.00 | 1.00 | 2.51 | 9.37 |
|  | 13.75 | 1.25 | 2.13 | 7.73 |
|  | 13.50 | 1.50 | 1.87 | 5.82 |
| 2.00 | 18.00 | 0 | 3.42 | 11.95 |
|  | 16.75 | 1.25 | 1.82 | 5.66 |
| 8.00 | 12.00 | 0 | 9.04 | >20 |
|  | 10.75 | 1.25 | 3.23 | 9.99 |

*bST: abbreviation of bovine somatotropin

EXAMPLE 2

Following the procedure as described in Example 1 except that isopropyl alcohol was used as lubricant, the composition was prepared and the syringeability was measured. The results were shown in Table 2.

TABLE 2

| Amount of *bST(g) | Amount of vitamin E acetate (g) | Amount of isopropyl alcohol (g) | Syringeability(kgf) Ambient temp. | Cold temp. |
|---|---|---|---|---|
| 5.00 | 15.00 | 0 | 5.24 | 14.76 |
|  | 14.50 | 0.50 | 2.78 | 9.74 |
|  | 14.00 | 1.00 | 1.83 | 4.67 |
|  | 13.50 | 1.50 | 1.65 | 2.90 |

*bST: abbreviation of bovine somatotropin

EXAMPLE 3

Following the procedure as described in Example 1 except that ethyl alcohol was used as lubricant, the composition was prepared and the syringeability was measured. The results were shown in Table 3.

TABLE 3

| Amount of *bST (g) | Amount of vitamin E acetate (g) | Amount of ethyl alcohol (g) | Syringeability(kgf) Ambient temp. | Cold temp. |
|---|---|---|---|---|
| 5.00 | 15.00 | 0 | 5.24 | 14.76 |
|  | 14.50 | 0.50 | 4.39 | 14.29 |
|  | 14.00 | 1.00 | 2.94 | 12.84 |
|  | 13.50 | 1.50 | 2.00 | 8.71 |

*bST: abbreviation of bovine somatotropin

EXAMPLE 4

Following the procedure as described in Example 1 except that ethyl oleate was used as lubricant, the composition was prepared and the syringeability was measured. The results were shown in Table 4.

TABLE 4

| Amount of *bST (g) | Amount of vitamin E acetate (g) | Amount of ethyl oleate (g) | Syringeability(kgf) Ambient temp. | Cold temp. |
|---|---|---|---|---|
| 5.00 | 15.00 | 0 | 5.24 | 14.76 |
|  | 14.00 | 1.00 | 2.33 | 9.48 |
|  | 13.75 | 1.25 | 2.47 | 7.99 |
|  | 13.50 | 1.50 | 2.15 | 5.51 |
|  | 13.00 | 2.00 | 1.70 | 4.07 |
|  | 12.00 | 3.00 | 1.58 | 2.12 |

*bST: abbreviation of bovine somatotropin

EXAMPLE 5

Following the procedure as described in Example 1 except that benzyl benzoate was used as lubricant, the composition was prepared and the syringeability was measured. The results were shown in Table 5.

TABLE 5

| Amount of *bST (g) | Amount of vitamin E acetate (g) | Amount of benzyl benzoate (g) | Syringeability(kgf) Ambient temp. | Cold temp. |
|---|---|---|---|---|
| 5.00 | 15.00 | 0 | 5.24 | 14.76 |
|  | 14.00 | 1.00 | 2.83 | 10.48 |
|  | 13.00 | 2.00 | 2.06 | 7.55 |
|  | 12.75 | 2.25 | 2.04 | 7.11 |
|  | 12.50 | 2.50 | 1.98 | 4.79 |
|  | 12.00 | 3.00 | 1.82 | 3.98 |

*bST: abbreviation of bovine somatotropin

EXAMPLE 6

Following the procedure as described in Example 1 except that Bridge 30 was used as lubricant, the composition was prepared and the syringeability was measured. The results were shown in Table 6.

TABLE 6

| Amount of *bST (g) | Amount of vitamin E acetate (g) | Amount of Bridge 30 (g) | Syringeability(kgf) Ambient temp. | Cold temp. |
|---|---|---|---|---|
| 5.00 | 15.00 | 0 | 5.24 | 14.76 |
|  | 12.00 | 3.00 | 1.93 | 4.24 |

*bST: abbreviation of bovine somatotropin

EXAMPLE 7

Following the procedure as described in Example 1 except that oleic acid was used as lubricant, the composition was prepared and the syringeability was measured. The results were shown in Table 7.

TABLE 7

| Amount of *bST (g) | Amount of vitamin E acetate (g) | Amount of oleic acid (g) | Syringeability(kgf) Ambient temp. | Cold temp. |
|---|---|---|---|---|
| 5.00 | 15.00 | 0 | 5.24 | 14.76 |
|  | 12.00 | 3.00 | 1.72 | 4.20 |

*bST: abbreviation of bovine somatotropin

EXAMPLE 8

Following the procedure as described in Example 1 except that GLYCOFUROL™ was used as lubricant, the composition was prepared and the syringeability was measured. The results were shown in Table 8.

TABLE 8

| Amount of *bST (g) | Amount of vitamin E acetate (g) | Amount of GLYCOFUROL ™ (g) | Syringeability(kgf) Ambient temp. | Cold temp. |
|---|---|---|---|---|
| 5.00 | 15.00 | 0 | 5.24 | 14.76 |
|  | 14.00 | 1.00 | 3.10 | 9.95 |
|  | 13.75 | 1.25 | 2.63 | 9.56 |
|  | 13.50 | 1.50 | 2.28 | 8.61 |
|  | 13.25 | 1.75 | 2.05 | 7.56 |
|  | 13.00 | 2.00 | 2.06 | 5.61 |
|  | 12.00 | 3.00 | 1.72 | 3.32 |

*bST: abbreviation of bovine somatotropin

EXAMPLE 9

Following the procedure as described in Example 1 except that polyethylene glycol 400 dimethylether was used as lubricant, the composition was prepared and the syringeability was measured. The results were shown in Table 9.

TABLE 9

| Amount of *bST (g) | Amount of vitamin E acetate (g) | Amount of polyethylene glycol 400 dimethylether (g) | Syringeability(kgf) Ambient temp. | Cold temp. |
|---|---|---|---|---|
| 5.00 | 15.00 | 0 | 5.24 | 14.76 |
|  | 14.25 | 0.75 | 3.15 | 11.29 |
|  | 13.50 | 1.50 | 2.48 | 6.58 |
|  | 12.00 | 3.00 | 1.62 | 2.97 |

*bST: abbreviation of bovine somatotropin

EXAMPLE 10

Following the procedure as described in Example 1 except that benzyl alcohol was used as lubricant and a mixture of vitamin E acetate and vitamin A acetate(1 g=2,800,000 IU, Sigma. U.S.A.) was used as vitamin, the composition was prepared and the syringeability was measured. The results were shown in Table 10.

TABLE 10

| Amount of *bST (g) | Amount of vitamin E acetate (g) | Amount of vitamin A acetate (g) | Amount of benzyl alcohol (g) | Syringeability(kgf) Ambient temp. | Cold temp. |
|---|---|---|---|---|---|
| 5.00 | 13.20 | 1.80 | 0 | 5.19 | 14.82 |
|  | 12.60 | 0.90 | 1.50 | 2.16 | 5.61 |
|  | 12.20 | 1.80 | 1.00 | 2.16 | 8.82 |
|  | 11.70 | 1.80 | 1.50 | 2.04 | 5.69 |
|  | 10.70 | 1.80 | 2.50 | 1.92 | 2.89 |
|  | 8.35 | 5.40 | 1.25 | 2.06 | 5.64 |

*bST: abbreviation of bovine somatotropin

EXAMPLE 11

Following the procedure as described in Example 10 except that benzyl benzoate was used as lubricant, the composition was prepared and the syringeability was measured. The results were shown in Table 11.

TABLE 11

| Amount of *bST (g) | Amount of vitamin E acetate (g) | Amount of vitamin A acetate (g) | Amount of benzyl benzoate (g) | Syringeability(kgf) Ambient temp. | Cold temp. |
|---|---|---|---|---|---|
| 5.00 | 13.20 | 1.80 | 0 | 5.19 | 14.82 |
|  | 11.20 | 1.80 | 2.00 | 2.52 | 9.56 |
|  | 10.70 | 1.80 | 2.50 | 2.20 | 6.63 |
|  | 10.20 | 1.80 | 3.00 | 1.83 | 6.29 |

*bST: abbreviation of bovine somatotropin

EXAMPLE 12

Following the procedure as described in Example 10 except that a mixture of benzyl alcohol and benzyl benzoate was used as lubricant, the composition was prepared and the syringeability was measured. The results were shown in Table 12.

TABLE 12

| Amount of *bST (g) | Amount of vitamin E acetate (g) | Amount of vitamin A acetate (g) | Amount of benzyl alcohol (g) | Amount of benzyl benzoate (g) | Syringeability(kgf) Ambient temp. | Cold temp. |
|---|---|---|---|---|---|---|
| 5.00 | 13.20 | 1.80 | 0 | 0 | 5.19 | 14.82 |
|  | 11.70 | 1.80 | 1.00 | 0.50 | 2.16 | 6.96 |
|  | 11.20 | 1.80 | 1.00 | 1.00 | 1.63 | 6.71 |
|  | 13.00 | 0 | 1.00 | 1.00 | 1.61 | 5.16 |
|  | 10.70 | 1.80 | 1.00 | 1.50 | 1.67 | 4.67 |
|  | 10.20 | 1.80 | 1.00 | 2.00 | 1.53 | 3.43 |

*bST: abbreviation of bovine somatotropin

EXAMPLE 13

Following the procedure as described in Example 10 except that ethyl oleate was used as lubricant and vitamin A palmitate(1 g=1,700,000 IU, ROCHE, Switzerland) instead of vitamin A acetate was used, the composition was prepared and the syringeability was measured. The results were shown in Table 13.

TABLE 13

| Amount of *bST (g) | Amount of vitamin E acetate (g) | Amount of vitamin A palmitate (g) | Amount of ethyl oleate (g) | Syringeability(kgf) Ambient temp. | Cold temp. |
|---|---|---|---|---|---|
| 5.00 | 12.00 | 3.00 | 0 | 3.56 | 13.86 |
|  | 10.00 | 5.00 | 0 | 3.27 | 12.22 |
|  | 11.00 | 3.00 | 1.00 | 2.01 | 6.23 |
|  | 10.00 | 3.00 | 2.00 | 1.62 | 2.82 |

*bST: abbreviation of bovine somatotropin

EXAMPLE 14

100 ml of bovine somatotropin(LG Chemical Ltd. Biotech Research Institute) solution(130.5 mg/ml) was mixed with 26.1 g of lecithin by using a homogenizer for 30 minutes. Then, the mixture was ground in a microfluidizer to make particles of 200 nm or below size of diameter. The suspension was filtrated through a filter of 0.22 $\mu$m pore size for sterilization, transferred into one lyophilization tray and lyophilized in a freeze-dryer for about 48 hours. The lyophilized powder was ground using an airjet mill to make particles of average 8 $\mu$m size of diameter. Thus obtained bovine somatotropin in a powder form had 1.6% of water content, which is measured in a heating-type moisture analyzer.

Using the lyophilized lecithin-bovine somatotropin powder, the composition was prepared and the syringeability was measured according to the procedure as described in Example 1 except that each amount was used as described below in Table 14. The results were shown in Table 14.

TABLE 14

| Amount of *bST (g) | Amount of lecithin (g) | Amount of vitamin E acetate (g) | Amount of benzyl alcohol (g) | Syringeability(kgf) Ambient temp. | Cold temp. |
|---|---|---|---|---|---|
| 5.00 | 1.00 | 14.00 | 0 | 4.97 | 15.25 |
|  | 1.00 | 12.75 | 1.25 | 2.83 | 10.12 |

*bST: abbreviation of bovine somatotropin

EXAMPLE 15

Animal tests were carried out using the compositions prepared as described below in Table 15. Female SD rats (180–220 g) of 8–9 weeks old were used. The interval between light and darkness in a room was 12 hours, and water and feed were freely accessible. 8 rats per one composition were used and 4 rats were included in a cage for an experiment. The rats were weighed before administration of the compositions. Then, the rats were randomly separated into the treated groups, based on the average body weight and the standard error. The body weight before administration of the composition was considered as a standard body weight of each rat. 80 mg of each composition (corresponding to 20 mg of bovine somatotropin) was subcutaneously injected into the abdominal region of each rat. Then, the rats were weighed at regular time everyday for 9 consecutive days. As a control group, 8 rats without any injection were weighed during the above test period by the same method. The cumulative mean weight gain of rats of each group was indicated in Table 16, which was measured after administration of the composition.

TABLE 15

| Composition No. | Amount of *bST (g) | Amount of vitamin E acetate (g) | Amount of vitamin A acetate (g) | Type and amount (g) of lubricant |
|---|---|---|---|---|
| 1 | 5.00 | 15.00 | 0 | 0 |
| 2 |  | 13.20 | 1.80 | 0 |
| 3 |  | 13.50 | 0 | Benzyl alcohol 1.50 |
| 4 |  | 11.70 | 1.80 | Benzyl alcohol 1.50 |
| 5 |  | 12.20 | 1.80 | Benzyl alcohol 1.00 |
| 6 |  | 14.00 | 0 | Ethyl oleate 1.00 |

*bST: abbreviation of bovine somatotropin

TABLE 16

| Day | Composition No. 1 | 2 | 3 | 4 | 5 | 6 | Negative control |
|---|---|---|---|---|---|---|---|
| 1 | 8.03 | 12.79 | 13.23 | 11.48 | 12.25 | 13.03 | 5.11 |
| 2 | 21.51 | 23.06 | 21.56 | 23.18 | 21.80 | 23.20 | 10.48 |
| 3 | 23.73 | 24.58 | 25.63 | 28.03 | 24.89 | 23.94 | 12.43 |
| 4 | 26.78 | 28.18 | 27.81 | 32.36 | 33.11 | 28.39 | 9.40 |
| 5 | 29.55 | 33.31 | 34.18 | 37.00 | 36.55 | 35.10 | 15.53 |
| 6 | 37.79 | 40.95 | 32.76 | 41.46 | 41.59 | 39.20 | 19.93 |
| 7 | 40.05 | 44.59 | 39.78 | 48.24 | 45.01 | 44.70 | 21.36 |
| 8 | 35.49 | 40.84 | 38.38 | 44.49 | 44.38 | 40.61 | 19.74 |
| 9 | 35.09 | 42.53 | 43.18 | 49.70 | 44.79 | 42.76 | 22.88 |

*Negative control: control that received no composition.
*Unit: g

EXAMPLE 16

Following the procedure as described in Example 15 except that compositions were prepared by mixing two kinds of lubricants as described below in Table 17, animal tests were carried out. The cumulative mean weight gain of rats of each group was indicated in Table 18, which was measured after administration of the composition.

TABLE 17

| Composition No. | Amount of *bST (g) | Amount of vitamin E acetate (g) | Amount of vitamin A acetate (g) | Type and amount (g) of lubricant |
|---|---|---|---|---|
| 1 | 5.00 | 13.20 | 1.80 | 0 |
| 2 |  | 11.20 | 1.80 | Benzyl alcohol 1.00, Benzyl benzoate 1.00 |

*bST: abbreviation of bovine somatotropin

TABLE 18

| | | Composition No. 1 | 2 | Negative control |
|---|---|---|---|---|
| Day | 1 | 10.63 | 10.86 | 1.71 |
|  | 2 | 19.95 | 18.89 | 7.14 |
|  | 3 | 24.08 | 23.45 | 7.45 |
|  | 4 | 28.10 | 27.73 | 9.51 |
|  | 5 | 32.36 | 33.20 | 13.55 |
|  | 6 | 38.18 | 39.63 | 17.46 |
|  | 7 | 42.44 | 43.09 | 15.64 |

TABLE 18-continued

| | | Composition No. | |
|---|---|---|---|
| | 1 | 2 | Negative control |
| 8 | 45.33 | 46.24 | 15.84 |
| 9 | 43.75 | 44.81 | 19.96 |

Negative control: control that received no composition.
*Unit: g

EXAMPLE 17

Following the procedure as described in Example 15 except that compositions were prepared as described below in Table 19 with the lecithin-bovine somatotropin prepared as described in Example 14 and genetically derived dwarf female rats(90–120 g) of 8 weeks old instead of normal rats were used, animal tests were carried out. The cumulative mean weight gain of rats of each group was indicated in Table 20, which was measured after administration of the composition.

TABLE 19

| Composition No. | Amount of *bST (g) | Amount of vitamin E acetate (g) | Amount of lecithin (g) | Type and amount (g) of lubricant |
|---|---|---|---|---|
| 1 | 5.00 | 15.00 | 0 | 0 |
| 2 | | 12.75 | 1.00 | Benzyl alcohol 1.25 |
| 3 | | 12.00 | 1.00 | Benzyl alcohol 1.00, Benzyl benzoate 1.00 |
| 4 | | 14.00 | 1.00 | 0 |

*bST: abbreviation of bovine somatotropin

TABLE 20

| | | Composition No. | | | | |
|---|---|---|---|---|---|---|
| | | 1 | 2 | 3 | 4 | Negative control |
| Day | 1 | 8.39 | 14.01 | 6.80 | 9.85 | 1.93 |
| | 2 | 12.49 | 17.59 | 13.48 | 11.57 | 3.45 |
| | 3 | 16.45 | 20.47 | 17.44 | 16.67 | 5.17 |
| | 4 | 20.25 | 27.63 | 23.58 | 22.87 | 7.37 |
| | 5 | 23.03 | 32.31 | 28.16 | 28.41 | 5.65 |
| | 6 | 28.87 | 35.99 | 31.14 | 31.71 | 8.29 |
| | 7 | 28.57 | 36.63 | 38.16 | 34.17 | 10.15 |
| | 8 | 26.21 | 36.19 | 40.56 | 33.55 | 11.61 |
| | 9 | 29.55 | 39.77 | 44.34 | 37.19 | 11.13 |

Negative control: control that received no composition.
*Unit: g

As shown above in the Tables 16, 18 and 20, it was confirmed that the body weight of the treated group with the composition of the present invention according to the Examples 15–17, increased more than about 20 g than that of the negative control group at the 9$^{th}$ day after administration of the composition, the composition of the present invention had a biological effect equivalent or more to that of the composition without any lubricant, and the composition of the present invention had improved syringeability that might maximize the convenience of the dairy farmer who administers the composition into animals.

Although the present invention has been described in detail with reference to the above specific embodiments, other embodiments are possible. Therefore, it should be apparent to those skilled in the art that various modifications and changes thereof can be made without departing from the spirit and scope of the invention and that such modifications and changes be included in the scope of the following claims.

What is claimed is:

1. A syringeable and injectable composition which consists of somatotropin, a lipid-soluble vitamin, and a pharmaceutically acceptable lubricant, and wherein the somatotropin is present in an amount of from 10 to 50% by weight, based on the total weight of the composition.

2. The composition according to claim 1, wherein the somatotropin is produced by recombinant DNA technology.

3. The composition according to claim 1 in suspension form.

4. The composition according to claim 3, wherein the lipid-soluble vitamin is vitamin A, a vitamin A derivative, vitamin E or a vitamin E derivative.

5. The composition according to claim 4, wherein the vitamin A or its derivative is present in an amount of from 100,000 to 5,000,000 vitamin A units per 1 g of somatotropin.

6. The composition according to claim 4, wherein the vitamin E or its derivative is present in an amount of from 500 to 12,000 vitamin E units per 1 g of somatotropin.

7. The composition according to claim 1, in fluid form and wherein the pharmaceutically acceptable lubricant is one which can be mixed with the lipid-soluble vitamin.

8. The composition according to claim 7, wherein the pharmaceutically acceptable lubricant is an alcohol or an alcohol derivative; an ester of fatty acid and an alcohol; an unsaturated fatty acid; an ester of an acid and an aromatic alcohol; or another material selected from the group consisting of polyoxyethylene alkyl ether and tetrahydrofurfuryl alcohol polyethylene glycol ether, which can be mixed with the lipid-soluble vitamin.

9. The composition according to claim 8, wherein the alcohol is a liquid selected from the group consisting of benzyl alcohol, ethyl alcohol, isopropyl alcohol and butyl alcohol.

10. The composition according to claim 8, wherein the ester of a fatty acid and an alcohol is a liquid selected from the group consisting of ethyl oleate, isopropyl myristate, isopropyl laurate, isopropyl lanolate, and isopropyl palmitate.

11. The composition according to claim 8, wherein the unsaturated fatty acid is a liquid selected from the group consisting of oleic acid, linoleic acid, and linolenic acid.

12. The composition according to claim 8, wherein the ester of an acid and an aromatic alcohol is benzyl benzoate.

13. The composition according to claim 7, wherein the lubricant is present in an amount of from 0.5 to 25% by weight based on the total weight of the composition.

14. The composition according to claim 7, wherein the pharmaceutically acceptable lubricant is an alcohol or an alcohol derivative.

15. The composition according to claim 7, wherein the pharmaceutically acceptable lubricant is an ester of a fatty acid and an alcohol.

16. The composition according to claim 7, wherein the pharmaceutically acceptable lubricant is an unsaturated fatty acid.

17. The composition according to claim 7, wherein the pharmaceutically acceptable lubricant is an ester of an acid and an aromatic alcohol.

18. The composition according to claim 7, wherein the pharmaceutically acceptable lubricant is a polyoxyethylene alkyl ether which can be mixed with the lipid-soluble vitamin.

19. The composition according to claim 7, wherein the pharmaceutically acceptable lubricant is a tetrahydrofurfuryl alcohol polyethylene glycol ether which can be mixed with the lipid-soluble vitamin.

20. The composition according to claim 7, wherein the pharmaceutically acceptable lubricant is a derivative of polyethylene glycol and glycerin, which can be mixed with the lipid-soluble vitamin.

* * * * *